United States Patent
Stone et al.

(10) Patent No.: US 6,949,936 B2
(45) Date of Patent: Sep. 27, 2005

(54) METHOD AND APPARATUS FOR THE DEBRIS PARTICULATE CHARACTERIZATION IN LUBRICANTS

(75) Inventors: Richard Stone, Merseyside (GB); Richard Mark Dowdeswell, Cheshire (GB); Mohammed El Hassan Amrani, Manchester (GB)

(73) Assignee: Kaiku Limited, Manchester (GB)

( * ) Notice: Subject to any disclaimer, the term of this patent is extended or adjusted under 35 U.S.C. 154(b) by 25 days.

(21) Appl. No.: 10/204,201

(22) PCT Filed: Feb. 16, 2001

(86) PCT No.: PCT/GB01/00636

§ 371 (c)(1),
(2), (4) Date: Oct. 28, 2002

(87) PCT Pub. No.: WO01/61339

PCT Pub. Date: Aug. 23, 2001

(65) Prior Publication Data

US 2003/0132740 A1 Jul. 17, 2003

(30) Foreign Application Priority Data

Feb. 16, 2000 (GB) .............................................. 0003442

(51) Int. Cl.$^7$ ............................................... G01R 27/04
(52) U.S. Cl. ....................................... 324/633; 324/698
(58) Field of Search ........................ 73/865.4; 324/71.1, 324/71.4, 633, 553, 639, 645, 658; 340/631, 450.3

(56) References Cited

U.S. PATENT DOCUMENTS

| 3,981,584 A | | 9/1976 | Guymer |
|---|---|---|---|
| 5,357,197 A | * | 10/1994 | Sorkin .......................... 324/204 |
| 5,357,497 A | | 10/1994 | Ogawa |
| 5,604,441 A | | 2/1997 | Freese, V et al. |
| 5,674,401 A | | 10/1997 | Dickert et al. |
| 5,754,055 A | * | 5/1998 | McAdoo et al. ............ 324/636 |
| 6,255,954 B1 | * | 7/2001 | Brown et al. ............... 340/603 |
| 2004/0239344 A1 | * | 12/2004 | Hu ............................... 324/698 |

FOREIGN PATENT DOCUMENTS

WO WO 00/72005 11/2000

* cited by examiner

*Primary Examiner*—Anjan Deb
*Assistant Examiner*—Walter Benson
(74) *Attorney, Agent, or Firm*—Oppenheimer Wolff & Donnelly LLP

(57) ABSTRACT

The present invention relates to an apparatus and method for measuring a particulate characteristic of a particulate-containing fluid, in particular for monitoring the particulate content of lubricating or hydraulic fluids in a mechanical system in order to diagnose component failure.

25 Claims, 7 Drawing Sheets

METHOD AND APPARATUS FOR THE DEBRIS PARTICULATE CHARACTERIZATION IN LUBRICANTS

BACKGROUND OF THE INVENTION

The present invention relates to an apparatus and method for measuring a particulate characteristic of a particulate-containing fluid, in particular for monitoring the particulate content of lubricating or hydraulic fluids in a mechanical system in order to diagnose component failure.

In many industries (in particular the aircraft industry), the need to diagnose impending mechanical failure is paramount. Currently, lubricating fluids may be tested for chemical or physical indicators of engine stress such as expenditure of additives, presence of water or changes in the concentration of metal particles. Analysis of wear debris in lubricating fluid and of the chemical properties of the fluid are normally carried out periodically (e.g., during routine maintenance).

Techniques commonly used to detect changes in the characteristics of wear particles include ferrography, emission spectroscopy, magnetic chip detection, x-ray fluorescence, ultra-sonic reflectometry and particle size analysis. Although in-line monitors such as magnetic chip detectors are in widespread use, these are generally inadequate as they are insensitive to particles smaller than a few hundred micrometers and therefore are unable to reliably monitor lubricating fluids in real time.

Particle size distribution analysis is usually performed by taking a sample of the fluid (e.g., oil) and passing it through a filter of known size. By either monitoring the flow rate across the filter or by tracking the pressure drop across it, it is possible to determine the particle size distribution in the fluid. An example of such a system is disclosed in U.S. Pat. No. 5,095,740.

In practice, measurements of particle size distribution are conducted on a regular basis on conventional hydraulic systems. However the determination of particle size distribution is a labor intensive activity and therefore is in general only performed periodically. For example, particle size distribution may be measured on a monthly basis and preventative measures taken as and when the oil quality data indicates that action is required. However, with measurements conducted so infrequently, there exists the real possibility of serious mechanical failure in the interim period.

U.S. Pat. No. 5,754,055 describes a method for determining the quality of hydraulic oil by interrogating a resonator cavity at microwave frequencies. By measuring the microwave resonant frequency and "quality factor" (a measure of the sharpness of the resonant microwave peak), various characteristics may be determined such as chemical concentration and debris concentration. However, this method suffers the drawback that it requires the insertion of a specially designed resonator cavity into the flow circuit.

The present invention seeks to address the limitations of the prior art by providing a method and apparatus for reliably and rapidly measuring a particulate characteristic of a particulate-containing fluid. In particular, the apparatus is able to monitor changes in particle size distribution of a fluid in real time. As such, the apparatus permits on-line diagnosis of component failure in a mechanical system, while requiring only minor modification to the system itself.

Thus viewed from one aspect the present invention provides a method for measuring a particulate characteristic of a particulate-containing fluid (e.g., a liquid), said method comprising the steps of:

applying an electrical signal at one or more frequencies to the fluid;

measuring an impedance quantity characteristic of the fluid at the one or more frequencies; and deducing the particulate characteristic from the measured impedance quantity.

The method of the invention is useful in static or dynamic fluid systems. The particulate-containing fluid may comprise a lubricating fluid or hydraulic fluid (e.g., an oil). As such the method is of particular interest to the aircraft and automotive industries. However, the method is equally of interest in the mining, mineral processing and milling industries.

The method of the invention may be used to deduce a qualitative or quantitative particulate characteristic of the fluid. For example, the qualitative or quantitative particulate characteristic may be the presence or absence of the particulate (qualitative), the extent of the presence of the particulate (quantitative), a change in the presence of the particulate (qualitative) or the extent of a change in the presence of the particulate (quantitative). Preferably, the particulate characteristic of the fluid is a physical indicator of the status of the mechanical system in which the fluid is present.

Preferably, the method may be used to deduce the presence (or absence) of a particulate in the fluid.

Preferably, the method may be used to deduce the amount (e.g., concentration) of a particulate in the fluid. Particularly preferably, the method may be used to deduce the particle size distribution (e.g., the number of particles above a certain size).

Preferably, the method may be used to deduce changes in the amount (e.g., concentration) of a particulate in the fluid (e.g., changes in the particle size distribution).

A preferred embodiment of the method of the invention comprises the steps of:

measuring at the one or more frequencies the impedance quantity characteristic of the particulate-containing fluid at a time $t_1$;

measuring at the one or more frequencies the impedance quantity characteristic of the particulate-containing fluid at a time $t_2$;

deducing a change in the characteristic of the particulate-containing fluid between time $t_1$ and $t_2$; and correlating the change in the characteristic of the particulate-containing fluid with a change in the fluid environment.

In a particularly preferred embodiment, the impedance quantity may be measured at any number of specific times (t) over an extended temporal range. Especially preferably the impedance quantity may be measured continuously so as to advantageously provide real time analysis of the fluid environment and diagnosis of any failure of the mechanical system of which the fluid environment is a part.

A preferred embodiment of the method of the invention comprises the initial steps of:

measuring an impedance quantity at one or more frequencies of a calibrant particulate-containing fluid; and correlating the measured impedance quantity with a particulate characteristic of the calibrant particulate-containing fluid, wherein the particulate characteristic of the calibrant particulate-containing fluid is known.

Preferably, the calibrant particulate-containing fluid is a fluid containing a known particulate.

Preferably the calibrant particulate-containing fluid is a fluid containing a particulate at a known particulate concentration (e.g., particle size distribution).

By way of example, the impedance quantity may be measured at one or more frequencies (preferably including the resonant frequency) for a hydraulic fluid in a mechanical system over a typical maintenance cycle. The measurement may be correlated with the particle size distribution measured conventionally over that cycle in order to calibrate the hydraulic fluid. For subsequent maintenance cycles, on-line measurement of the impedance quantity at one or more frequencies (preferably including the resonant frequency) may be used (in place of conventional particle size distribution analysis) to deduce the particle size distribution. This final step may be conveniently carried out by interpolation. Methods of interpolating data will be familiar to those skilled in the art. They include inter alia look-up tables or the application of artificial neural network technology to "learn" the relationship between (for example) resonant frequency and number of particles.

In a preferred embodiment of the method of the invention, the electrical signal is applied to the particulate-containing fluid at a single frequency and the impedance quantity of the particulate-containing fluid is measured at that frequency. Preferably, the single frequency is at or near to the resonant frequency. A frequency at or near to the resonant frequency provides the largest variations in the measured impedance quantity and hence a more sensitive method.

A preferred embodiment of the method of the invention comprises applying an electrical signal to the particulate-containing fluid at each of a plurality of frequencies in a frequency range and measuring an impedance quantity at each of the plurality of frequencies in the frequency range. If desired, the plurality of frequencies in the range are sufficient in number to generate an impedance spectrum characteristic of the particulate-containing fluid. Particularly preferably, the frequency range includes a resonant frequency.

The impedance quantity may be for example the dissipation factor.

In an embodiment of the method of the invention, the electrical signal is a time varying electrical signal. Preferably, the time varying electrical signal is an alternating current (ac) signal. Preferably the electrical signal is a sine wave varying in current or voltage.

The measurement of the impedance quantity may comprise a time to frequency domain transformation of the time varying electrical signal. The steps involved in such a measurement will be generally familiar to those skilled in the art (see for example Perturbation Signals for System Identification, ed K Godfrey, Prentice Hill, 1993, UK). The time varying electrical signal may be periodic and may comprise any suitable function or code e.g., a pseudo random binary sequence (PRBS), a Golay code, a Walsh function, a Huffman sequence or any other suitable coded sequence. Other suitable signals, codes or methodologies such as white Gaussian noise or wavelet analysis may be employed and will be generally familiar to those skilled in the art (see for example Signal Processing Methods for Audio Images and Telecommunications, eds P M Clarkson and H Stork, Academic Press, London, 1995).

Viewed from a further aspect the present invention provides an apparatus for measuring a particulate characteristic of a particulate-containing fluid comprising:

electrical signal applying means adapted to apply an electrical signal at one or more frequencies to the fluid;

measuring means for measuring an impedance quantity characteristic of the fluid at the one or more frequencies; and means for deducing the particulate characteristic from the measured impedance quantity.

The apparatus of the invention is advantageously capable of providing a rapid (and if desired continuous) online physical indicator of fluid (e.g., oil) quality. For example, the apparatus may be positioned in situ as part of the fluid environment of a mechanical system (e.g., an engine or hydraulic system) where it is capable of advantageously indicating sudden changes within seconds of their occurrence. For example, the apparatus incorporated in an aircraft in this manner may allow an airline pilot to take evasive action in the event of catastrophic mechanical failure of the engine.

The apparatus of the invention is advantageously provided in portable form for in situ analysis. This enables on-line monitoring of lubricating or hydraulic fluids in a static or dynamic system.

In the apparatus of the invention, the electrical signal applying means is preferably adapted to apply a time varying electrical signal to the particulate-containing fluid at one or more frequencies in a frequency range (preferably including a resonant frequency). Preferably, the electrical signal applying means is capable of applying a time varying electrical signal which is periodic. Preferably, the electrical signal applying means is capable of applying an ac signal of variable frequency. Preferably the electrical signal applying means is capable of applying an electrical signal being a sine wave varying in current or voltage.

The electrical signal applying means may be capable of being positioned in direct or indirect electrical contact with the particulate-containing fluid.

The electrical signal applying means may comprise a means for varying the frequency of the electrical signal to apply the electrical signal at a plurality of frequencies in a range including the resonant frequency. The resonant frequency may be lowered or altered by the addition of further circuit elements. For example, the apparatus may further comprise at least one inductor or at least one quartz crystal resonator. Conveniently, the means for varying the resonant frequency is arranged so that the resonant frequency is below about 1 MHz. At such a resonant frequency, problems associated with instrumentation and digitisation are generally reduced.

The electrical signal applying means may comprise at least two electrodes. The electrodes may be capable of being positioned in direct or indirect electrical contact with the particulate-containing fluid. For example, one or more of the electrodes may comprise an outer insulating layer so that the electrodes are capable of being positioned in indirect electrical contact with the particulate-containing fluid.

Numerous electrode materials, sizes and configurations are suitable (as desired) for the preferred embodiment. Generally, the configuration and material may be tailored to the end use. For example, planar electrodes may be used (e.g., rectangular or half ring configurations as desired) and multiple electrode arrangements may be used. Modulation of the applied electrical field strength is possible to find the optimum working field strength or to provide additional information on the particulate-containing fluid.

The electrical signal applying means may comprise at least two windings. The windings may be capable of being positioned in direct or indirect electrical contact with the particulate-containing fluid.

In an embodiment of the invention, the electrical signal applying means comprises a probe adapted to be inserted into a mechanical system and to enable measurement of the impedance spectrum characteristic of particulate-containing fluid within the mechanical system.

In an embodiment of the apparatus of the invention, the measuring means may comprise an impedance analyzer.

In an embodiment of the apparatus of the invention, the measuring means may be capable of performing a time to frequency domain transformation of the time varying electrical signal.

Viewed from a yet further aspect the present invention provides the use of an apparatus as hereinbefore defined for diagnosing failure of a mechanical system.

BRIEF DESCRIPTION OF THE DRAWINGS

The present intention will now be described in a non-limitative sense with reference to the accompanying Figures in which.

DETAILED DESCRIPTION OF THE DRAWINGS

Figure 1:
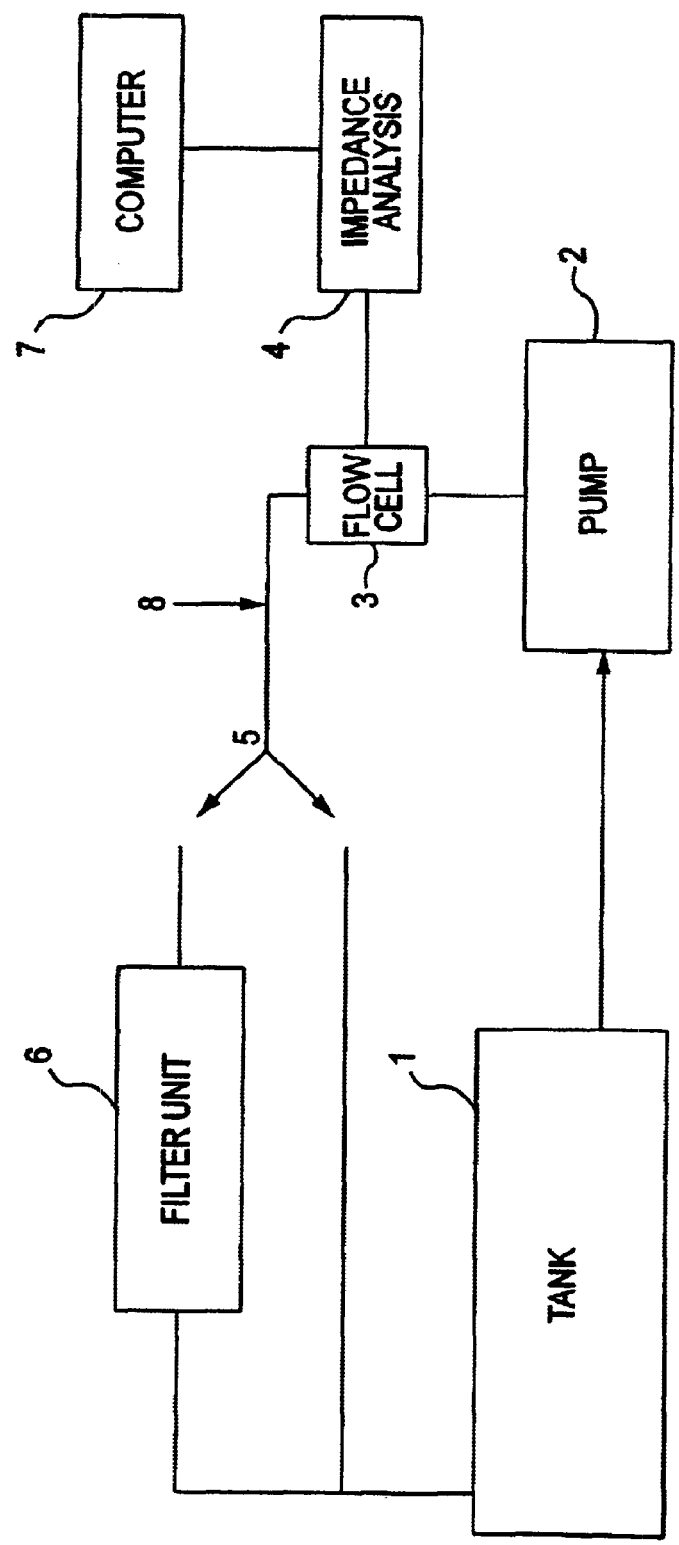
FIG. 1 illustrates schematically an experimental arrangement used to demonstrate the method of the invention.

FIG. 1 illustrates schematically an experimental arrangement which was used to measure electrical impedance spectra and particle size distributions of various samples in order to demonstrate the principles of the method of the invention.

A ten liter tank 1 was filled with five liters of standard engine oil. The oil was circulated by means of a pump 2 via a flow cell 3 to a two-way valve 5. Depending upon the position of the valve, the oil was either directed back to the tank 1 or through a one micron filter unit 6 before being returned to the tank 1. The flow cell was of the type disclosed in WO-A-98/46985 and was connected to a Hewlett Packard 4192A impedance analyser 4 which was connected to a personal computer 7.

A port 8 was incorporated into the arrangement so that oil samples could be withdrawn for analysis or to which a particle sizing device could be attached. During these analyses, a digital CONTAM-ALERT (DCA) unit (available from EntekIRD Limited, Bumpers Lane, Sealand Industrial Estate, Chester, England, CH1 4LT) was used to determine the particle size distribution of the oil at various stages of the experiment (i.e., the particle size distribution of each sample). With the arrangement set in the re-circulating position, the oil which flowed through the circuit was analyzed by the impedance analyzer 4 and the impedance spectrum of each sample (including the resonant frequency) was recorded and transmitted to the personal computer 7 for analysis and storage.

Figure 2:
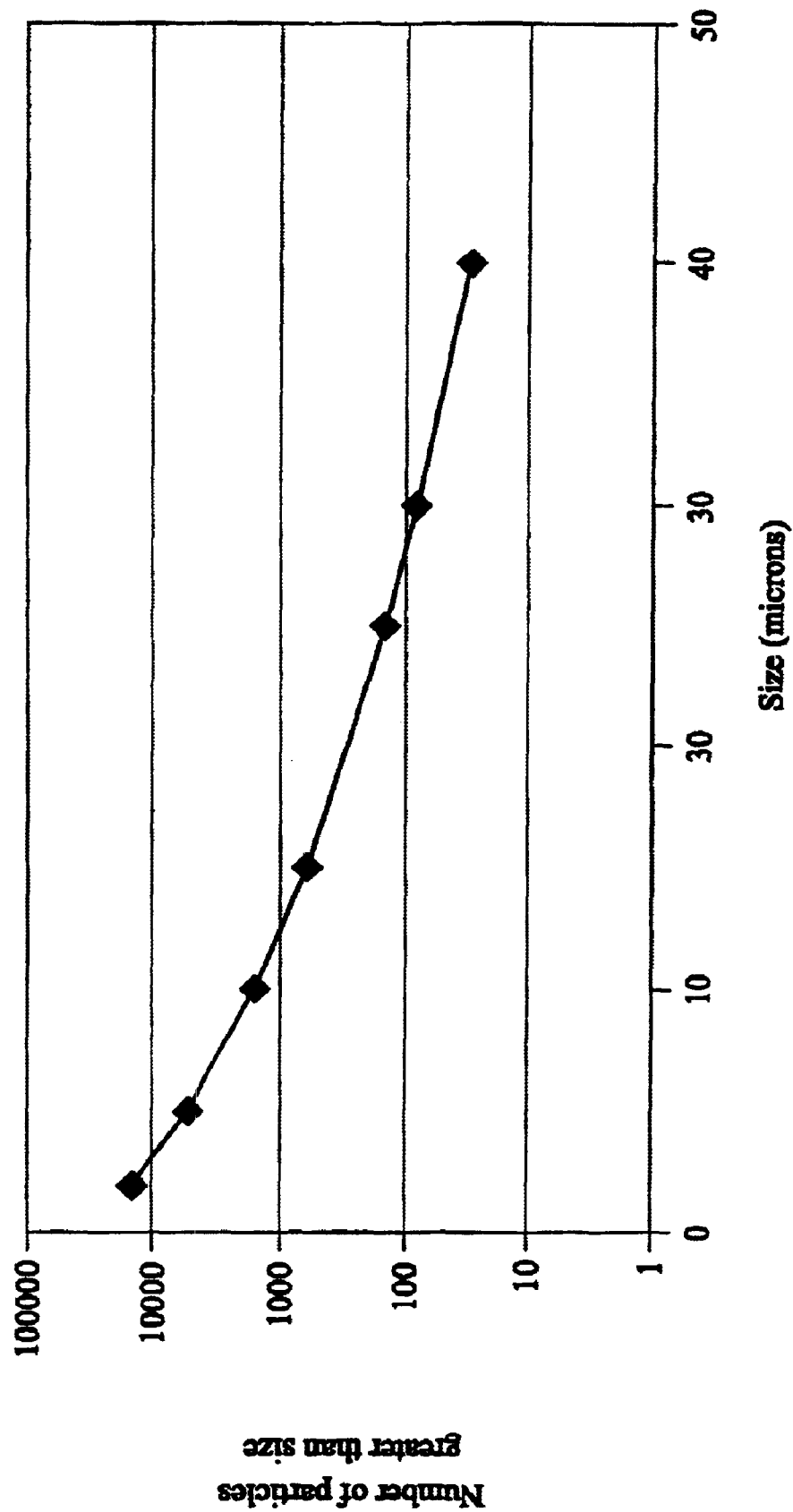
FIG. 2 illustrates particle size distribution as measured conventionally.
Figure 3:
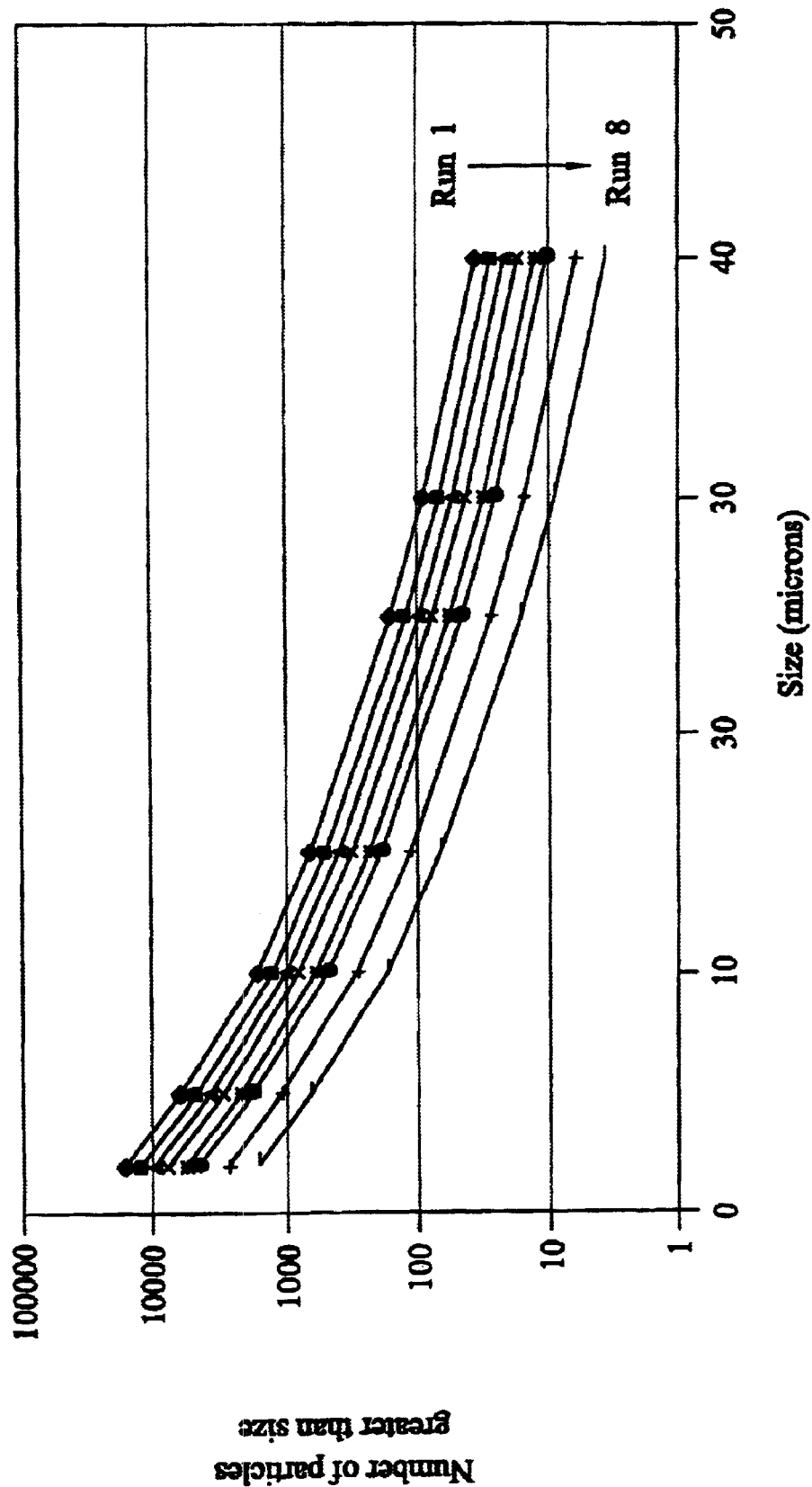
FIG. 3 illustrates particle size distribution measured conventionally after filtering.

Into the clean oil were deposited various metallic and non-metallic particles in order to give the particle size distribution illustrated in FIG. 2 (as determined using the DCA). The re-circulating flow was diverted for 30 seconds through the filter before being returned to the re-circulation mode. The particle size distribution was again determined using the DCA unit. This procedure was then repeated a further six times. FIG. 3 illustrates the particle size distribution for all eight samples as the log (base 10) of the number of particles versus particle size fraction in microns.

Figure 4:
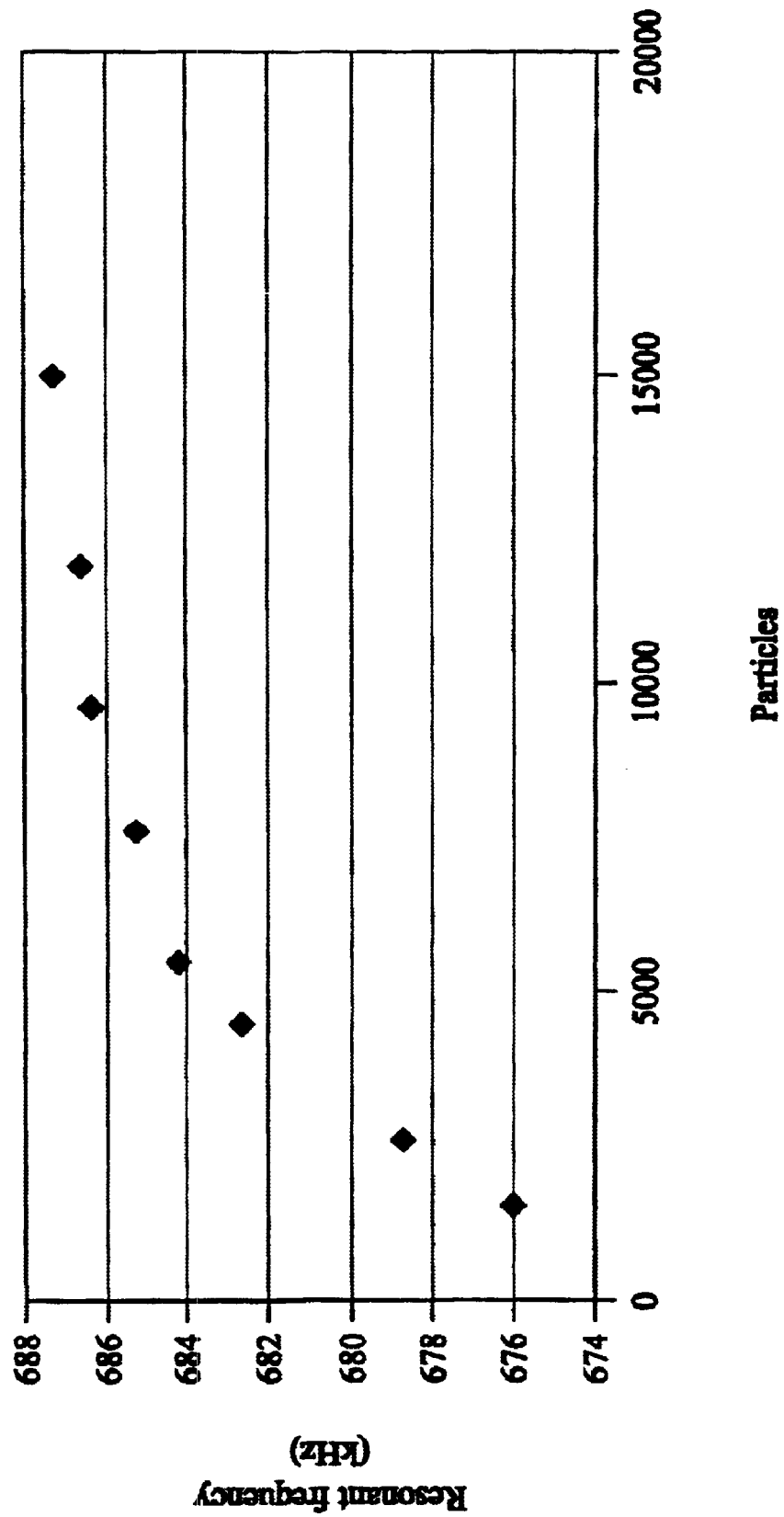
FIGS. 4–7 illustrate the resonant frequency of each of eight oil samples as a function of the number of particles over a certain size.
Figure 5:
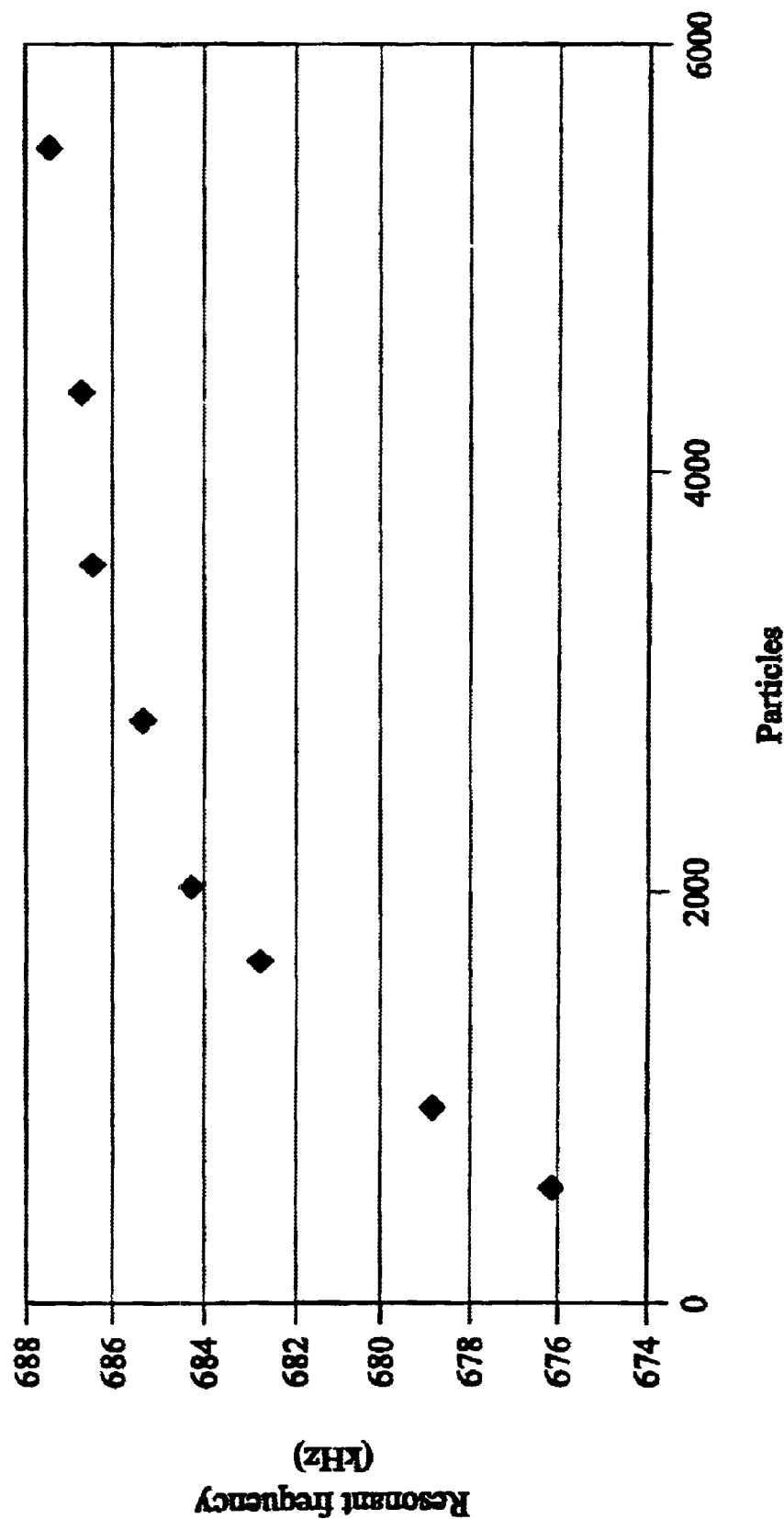
Figure 6:
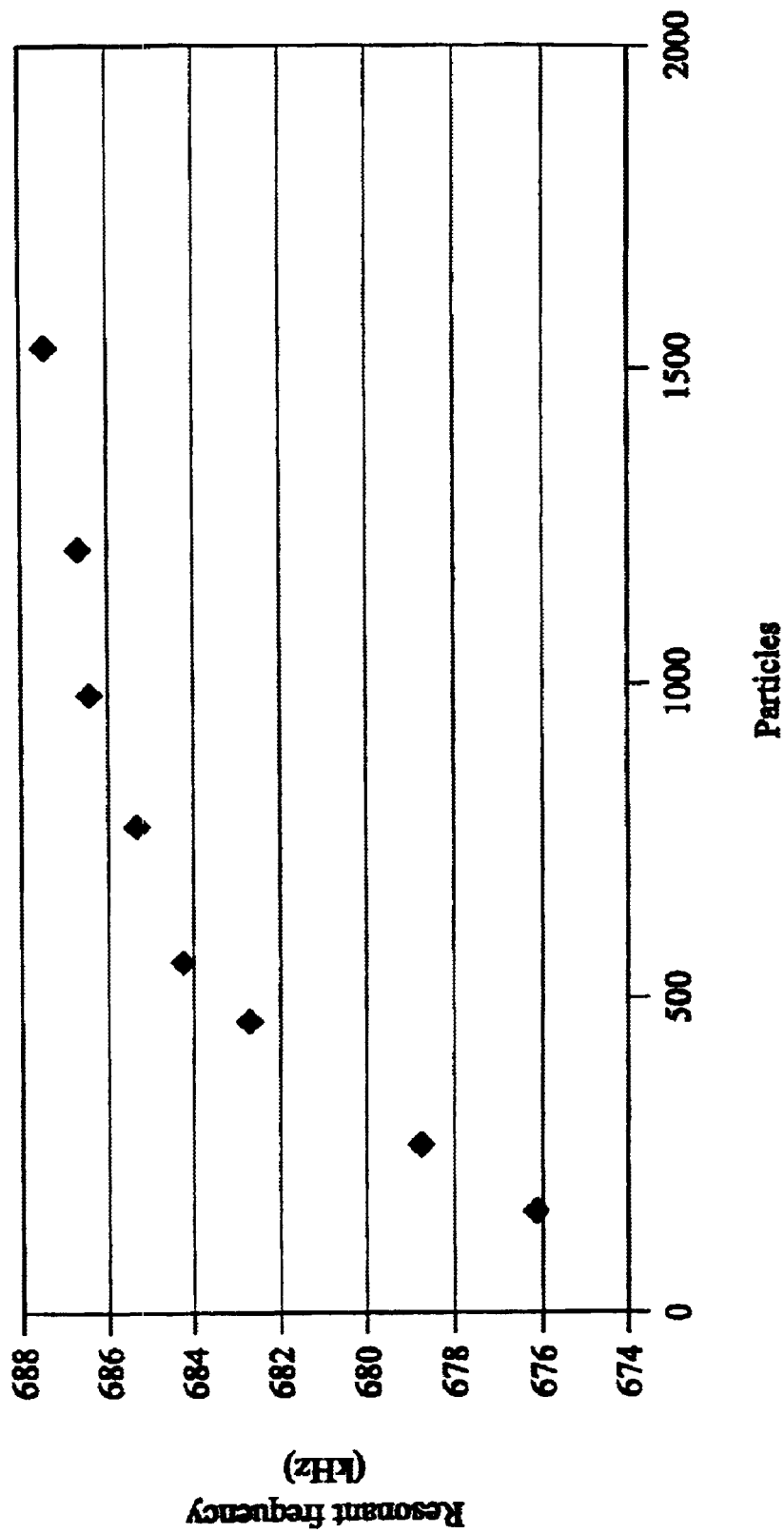
Figure 7:
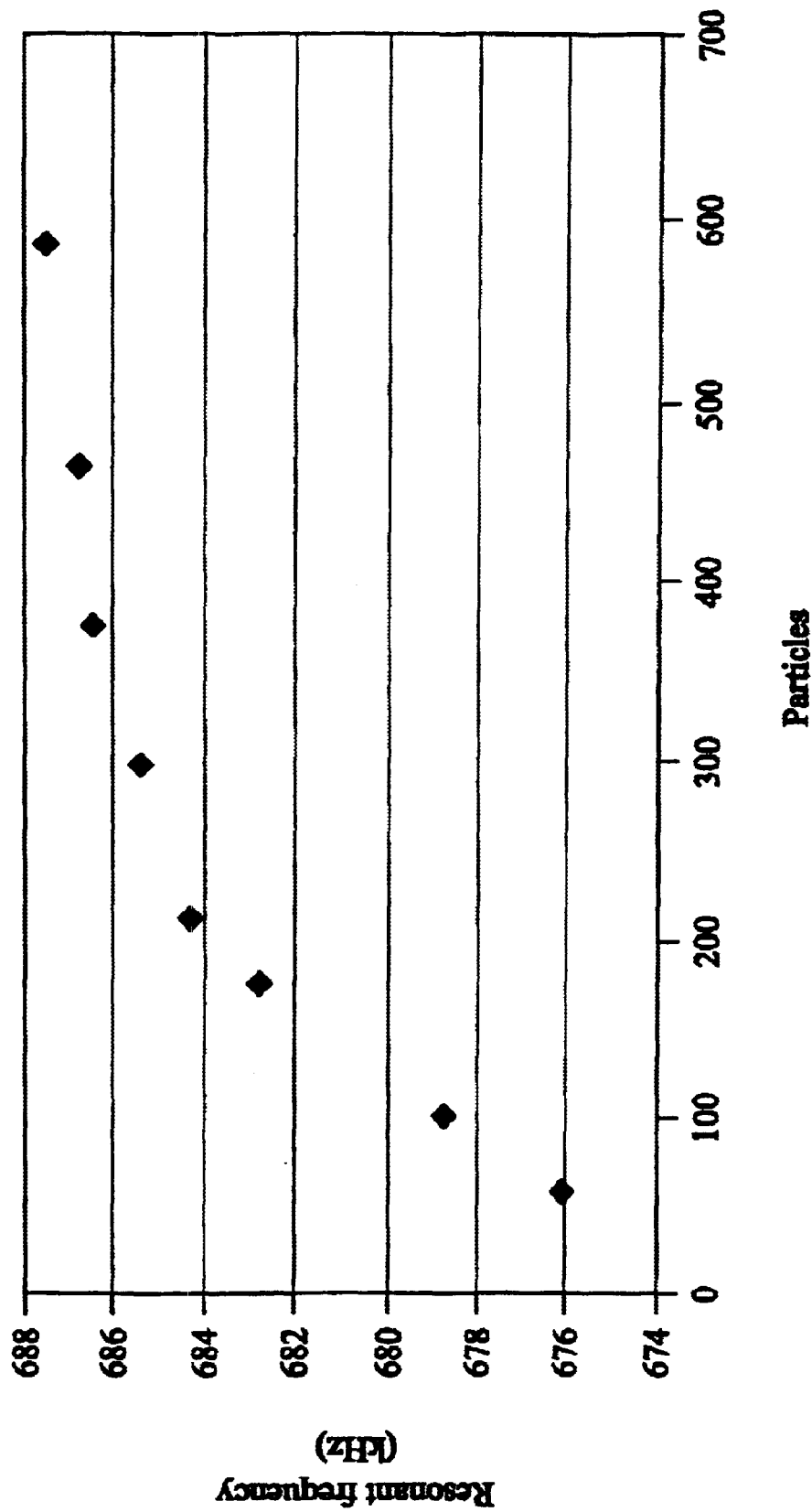

FIGS. 4–7 illustrate the resonant frequency of each of the eight oil samples as a function of the number of particles greater than a certain size. For example, FIG. 4 illustrates the resonant frequency of the oil as a function of the number of particles greater than 2 microns. FIGS. 5, 6 and 7 represent the 5, 10 and 15 micron levels, respectively. A mathematical model may be calculated to describe the data recorded in the various Figures which would aid subsequent calculations.

The following is an example to illustrate how an unknown particle size distribution may be deduced from a measured resonant frequency. This is based upon the data obtained using the arrangement described above.

A resonant frequency of 680 kHz is recorded for an oil sample. By reference to FIG. 4 (or an equation calculated to describe the measured impedance data), it is possible to interpolate from this resonant frequency the number of particles present. This gives an approximate value for the number of particles greater than 2 micron size of 3300. This procedure is repeated using FIGS. 5, 6 and 7 to obtain estimates of the number of particles greater than the 5, 10 and 15 micron threshold and hence the particle size distribution.

It will be apparent to a person skilled in the art that the eight curves illustrated in FIG. 3 follow the same general trend and that it is possible to model this data. The choice of mathematical model depends upon the data recorded but for this example an exponential curve such as the following form appears to fit the data well:

$$y = ce^{dx} \qquad \text{(equation 1)}$$

(where y represents the log of the number of particles, c and d represent constants and x represents the size in microns)

The measured impedance quantity may be used to read off from FIGS. 4–7 the number of particles y at a size z. For this, c and d may be calculated making it possible to estimate the number of particles in other size fractions.

What is claimed is:

1. A method for measuring a particulate characteristic of a fluid, said method comprising:

applying an electrical signal at each of a plurality of frequencies in a frequency range to a fluid, wherein the frequency range includes a resonant frequency;

measuring an impedance quantity characteristic of the fluid at each of the plurality of frequencies at a time $t_1$;

measuring at each of the plurality of frequencies the impedance quantity characteristic of the fluid at a time $t_2$;

deducing a change in a particulate characteristic of the fluid from the measured impedance quantity between $t_1$ and $t_2$; and correlating the change in the particulate characteristic of the fluid with a change in the fluid environment.

2. A method as claimed in claim 1 wherein the fluid is a liquid.

3. A method as claimed in claim 2 wherein the fluid is a lubricating fluid or hydraulic fluid.

4. A method as claimed in claim 1 wherein the particulate characteristic is selected from the group consisting of (a) the presence or absence of the particulate (b) the extent of the presence of the particulate (c) a change in the presence of the particulate and (d) the extent of a change in the presence of the particulate.

5. A method as claimed in claim 4 wherein the particulate characteristic of the fluid is a physical indicator of the status of a static or dynamic system in which the fluid is present.

6. A method as claimed in claim 4 wherein the particulate characteristic is the presence or absence of a particulate in the fluid.

7. A method as claimed in claim 1 wherein the particulate characteristic is the amount of a particulate in the fluid.

8. A method as claimed in claim 7 wherein the particulate characteristic is the particle size distribution.

9. A method as claimed in claim 1 wherein the particulate characteristic is a change in the particle size distribution.

10. A method as claimed in claim 1 further comprising:
measuring the impedance quantity at a number of discrete times over an extended temporal range.

11. A method as claimed in claim 10 further comprising:
measuring the impedance quantity continuously so as to provide real time analysis of the fluid environment.

12. A method as claimed in claim 1 further comprising the initial steps of:
applying an electrical signal at one or more frequencies to a calibrant fluid;
measuring an impedance quantity at one or more frequencies of the calibrant fluid; and
correlating the measured impedance quantity with a particulate characteristic of the calibrant fluid, wherein the particulate characteristic of the calibrant fluid is known.

13. A method as claimed in claim 12 wherein the calibrant fluid is a fluid containing a known particulate.

14. A method as claimed in claim 12 wherein the calibrant fluid is a fluid containing a particulate at a known particulate concentration.

15. A method as claimed in claim 12 wherein the calibrant fluid is a fluid containing a known particulate distribution.

16. A method as claimed in claim 1 wherein the electrical signal is applied to the fluid at a single frequency and the impedance quantity of the fluid is measured at that single frequency.

17. A method as claimed in claim 16 wherein the single frequency is at or near to the resonant frequency.

18. A method as claimed in claim 16 wherein the impedance quantity is a dissipation factor.

19. A method as claimed in claim 16 wherein the electrical signal is a time varying electrical signal.

20. A method as claimed in claim 1 wherein the plurality of frequencies in the frequency range are sufficient in number to generate an impedance spectrum characteristic to the fluid.

21. A method as claimed in claim 1 wherein the impedance quantity is a dissipation factor.

22. A method as claimed in claim 1 wherein the electrical signal is a time varying electrical signal.

23. An apparatus for measuring a particulate characteristic of a fluid comprising:
electrical signal applying means adapted to apply an electrical signal at each of a plurality of frequencies in a frequency range to a fluid, wherein the frequency range includes a resonant frequency;
measuring means for measuring an impedance quantity characteristic of the fluid at the plurality of frequencies; and
means for deducing the particulate characteristic from the measured impedance quantity wherein the electrical signal applying means comprises a probe adapted to be inserted into a mechanical system so as to enable measurement of the impedance spectrum characteristic of a fluid within the mechanical system and further wherein the electrical signal applying means is adapted to apply a time varying electrical signal to the fluid at one or more frequencies in a frequency range.

24. An apparatus as claimed in claim 23 comprising at least two electrodes capable of being positioned in direct or indirect electrical contact with the fluid.

25. An apparatus as claimed in claim 23 wherein the measuring means comprises an impedance analyser.

* * * * *